(12) United States Patent
Farazi et al.

(10) Patent No.: US 7,711,415 B1
(45) Date of Patent: May 4, 2010

(54) IMPLANTABLE DEVICES, AND METHODS FOR USE THEREWITH, FOR MONITORING SYMPATHETIC AND PARASYMPATHETIC INFLUENCES ON THE HEART

(75) Inventors: Taraneh Ghaffari Farazi, San Jose, CA (US); Gene A. Bornzin, Simi Valley, CA (US); Mark W. Kroll, Fremont, CA (US); Michael E. Benser, Valencia, CA (US); Kevin S. Jurkowski, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 643 days.

(21) Appl. No.: 11/557,814

(22) Filed: Nov. 8, 2006

(51) Int. Cl.
 *A61B 5/04* (2006.01)
(52) U.S. Cl. ...................................... 600/509
(58) Field of Classification Search ................ 600/509, 600/485, 515, 519; 607/9, 14, 17, 25
 See application file for complete search history.

(56) References Cited

U.S. PATENT DOCUMENTS

| | | | | |
|---|---|---|---|---|
| 5,682,901 | A * | 11/1997 | Kamen | 600/519 |
| 6,685,649 | B2 * | 2/2004 | Korhonen | 600/485 |
| 7,027,856 | B2 * | 4/2006 | Zhou et al. | 600/515 |
| 7,076,299 | B2 * | 7/2006 | Thong | 607/14 |
| 2007/0129763 | A1 * | 6/2007 | Cates | 607/9 |
| 2008/0269821 | A1 * | 10/2008 | Kullok et al. | 607/17 |
| 2008/0281247 | A1 * | 11/2008 | Tadokoro et al. | 604/5.01 |

* cited by examiner

*Primary Examiner*—George Manuel
*Assistant Examiner*—Robert N Wieland
(74) *Attorney, Agent, or Firm*—Theresa Takenchi; Steven M. Mitchell

(57) ABSTRACT

Provided herein are implantable devices, and methods for use therewith, that independently monitor levels of parasympathetic and sympathetic tone of a patient. In accordance with an embodiment, a cardiac electrogram (EGM) signal is sensed using implanted electrodes, cardiac intervals are measured within a portion of the sensed EGM signal, and levels of parasympathetic tone and sympathetic tone are independently assessed based on the measured cardiac intervals. This abstract is not intended to describe all of the various embodiments of the present invention.

20 Claims, 9 Drawing Sheets

FIG. 3A   Identification of anchor points
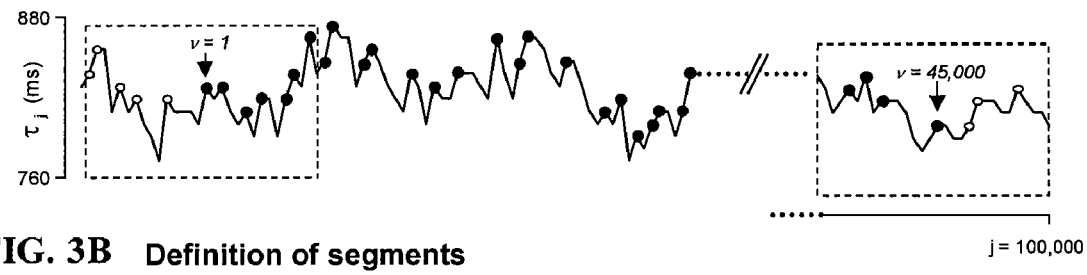
FIG. 3B   Definition of segments
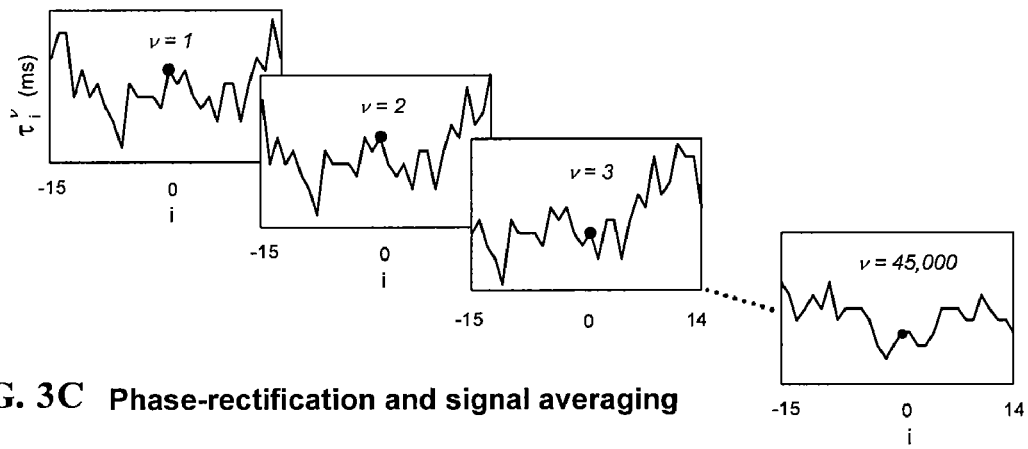
FIG. 3C   Phase-rectification and signal averaging
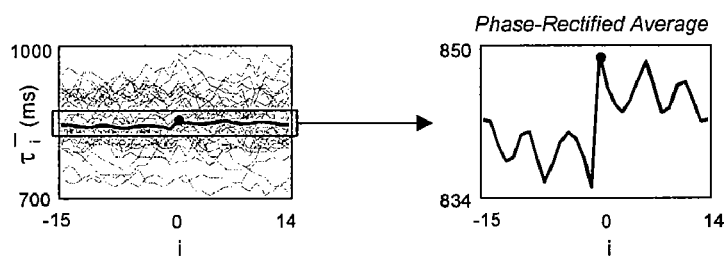

IMPLANTABLE DEVICES, AND METHODS FOR USE THEREWITH, FOR MONITORING SYMPATHETIC AND PARASYMPATHETIC INFLUENCES ON THE HEART

CROSS REFERENCE TO RELATED APPLICATIONS

The present invention relates to U.S. patent application Ser. No. 11/249,653, entitled "Implantable Devices, and Methods for Use Therewith, For Performing Cardiac and Autonomic Assessments Using Phase Rectified Signal Averaging," filed Oct. 12, 2005, which is incorporated herein by reference.

FIELD OF THE INVENTION

The present invention generally relates to an implantable cardiac device that can monitor a patient's heart. The present invention more particularly relates to such an implantable device capable of independently monitoring sympathetic and parasympathetic influences on the heart.

BACKGROUND

The autonomic nervous system has two components, including a sympathetic component that is relatively slow acting, and a parasympathetic component (also known as the vagal component) that provides a relatively faster response than the sympathetic component. A proper balance between the sympathetic and parasympathetic components of the autonomic nervous system is believed to be important. Accordingly, an indication of the balance of these components of the autonomic nervous system, which is sometimes referred to as "autonomic balance" or "sympathovagal balance", is sometimes used an indication of a patient's well-being.

Quantitative assessment of the autonomic nervous system's activity has largely been based on analysis of heart rate variability (HRV). In such techniques, a measure of sympathovagal balance is often given in terms of some form of standard deviation in RR intervals (e.g., SDNN, a time domain approach) or ratio of low to high frequency components of the power spectrum (the spectral approach).

More specifically, in one time domain approach, the standard deviation of RR intervals (SDNN) is measured. In this approach, an increase in SDNN is interpreted as an increased predominance of the sympathetic component (and a proportional decrease in the parasympathetic component), where a decrease in the SDNN is interpreted as an increased predominance of the parasympathetic component (and a proportional decrease in the parasympathetic component).

In one spectral approach, measures of normal RR intervals are converted into the frequency-domain so that its spectral frequency components can be analyzed. Two frequency bands are indicated as being of interest, including, e.g., a low frequency (LF) band (e.g., between 0.04 Hz and 0.14 Hz) and a high frequency (HF) band (e.g., between 0.15 Hz. and 0.40 Hz). The HF band of the R-R interval signal is believed to be influenced by only the parasympathetic component of the autonomic nervous system. The LF band of the R-R interval signal is believed to be influenced by both the sympathetic and parasympathetic components of the autonomic nervous system. Consequently, the ratio LF/HF is used as an indication of the autonomic balance between sympathetic and parasympathetic components of the autonomic nervous system. More specifically, an increase in the LF/HF ratio is interpreted as an increased predominance of the sympathetic component (and a proportional decrease in the parasympathetic component), where a decrease in the LF/HF ratio is interpreted as an increased predominance of the parasympathetic component (and a proportional decrease in the parasympathetic component).

A related time domain approach obtains a first measure that is believed to be influenced by only the parasympathetic component of the autonomic nervous system, and a second measure that is believed to be influenced by both the sympathetic and parasympathetic components of the autonomic nervous system. As in the above described spectral approach, a ratio is then taken of the two measures to obtain a measure of the autonomic balance between sympathetic and parasympathetic components of the autonomic nervous system. Similarly, an increase in the ratio is interpreted as an increased predominance of the sympathetic component (and a proportional decrease in the parasympathetic component), where a decrease in the ratio is interpreted as an increased predominance of the parasympathetic component (and a proportional decrease in the parasympathetic component).

Though useful in quantifying the sympathetic and parasympathetic balance, both frequency and time domain approaches that have been suggested do not provide information on the sympathetic and parasympathetic components independently. For example, decreased HRV can be described by either a decreased SDNN or increased LF/HF ratio. However, both of these measures are interpreted as being caused by either a decrease in parasympathetic tone (also referred to as vagal tone) or an increase in sympathetic tone. In other words, conventional approaches for quantifying the sympathetic and parasympathetic balance have assumed that as one component goes up, the other component goes proportionally down, and vice versa.

BRIEF SUMMARY OF THE INVENTION

Embodiments of the present invention enable the sympathetic and parasympathetic systems to be monitored independently.

Specific embodiments relate to independently monitoring the two systems using a Phase Rectified Signal Averaging (PRSA) technique. Use of this technique has been described in recent publications (e.g., *Circulation*, 2004. v. 110 no. 17 supp III, Abs. 2155) as being superior to using standard deviation of normal RR intervals (SDNN) and left ventricular ejection fraction (LVEF) for prediction of late mortality after a patient has experienced an acute myocardial infarction (AMI). Such publications explain that Holter recordings were obtained for a training sample of patients that survived an AMI. PRSA was then used to analyze the Holter recordings of the patients, to thereby predict which patients would experience late mortality (i.e., not survive) and which patient's would not experience later mortality (i.e., survive). Without elaboration, one such publication suggested that the PRSA technique may also be proposed for a variety of other applications.

Embodiments of the present invention relate to implantable devices, and methods for use therewith, that independently monitor levels of parasympathetic and sympathetic tone of a patient. In accordance with an embodiment, a cardiac electrogram (EGM) signal is sensed using implanted electrodes, cardiac intervals are measured within a portion of the sensed EGM signal, and levels of parasympathetic tone and sympathetic tone are independently assessed based on the measured cardiac intervals.

The level of parasympathetic tone can be assessed by determining the patient's diurnal variation of cardiac intervals based on the measured cardiac intervals, and assessing the level of parasympathetic tone based on the diurnal variation of cardiac intervals. Alternatively, the level of parasympathetic tone can be assessed by determining the patient's diurnal variation of heart rate based on the measured cardiac intervals, and assessing the level of parasympathetic tone based on the diurnal variation of heart rate. Another alternative is to identify each cardiac interval that is longer than the immediately preceding cardiac interval as being indicative of cardiac deceleration, and assessing the level of parasympathetic tone based on the cardiac intervals that are identified as being indicative of cardiac deceleration.

The level of sympathetic tone can be assessed by determining the patient's average cardiac interval based on the measured cardiac intervals, and assessing the level of sympathetic tone based on the determined average cardiac interval. Alternatively, the level of sympathetic tone can be assessed by determining the patient's average heart rate based on the measured cardiac intervals, and assessing the level of sympathetic tone based on the determined average heart rate. Another alternative is to identify each cardiac interval that is shorter than the immediately preceding cardiac interval as being indicative of cardiac acceleration, and assessing the level of sympathetic tone based on the cardiac intervals that are identified as being indicative of cardiac acceleration.

Further embodiments relate to producing an autonomic nervous system index (ANSi) value based on a normalized measure of an average deceleration segment and the normalized measure of an average acceleration segment.

Specific embodiments also relate to comparing assessed levels of parasympathetic and sympathetic tone for a patient with previously assessed levels parasympathetic and sympathetic tone for the patient to monitor changes in the patient's levels of parasympathetic and sympathetic tone.

This summary is not intended to be a complete description of, or limit the scope of, the invention. Alternative and additional features, aspects, and objects of the invention can be obtained from a review of the specification, the figures, and the claims.

BRIEF DESCRIPTION OF THE DRAWINGS

FIGS. 3A-3C are useful for explaining phase rectified signal averaging (PRSA) techniques. FIG. 3A illustrates an exemplary graph of beat numbers versus RR intervals that is produced from a portion of a cardiac signal. FIG. 3B illustrates exemplary segments of the cardiac signal that are centered around anchor points that are identified based on the graph of FIG. 3A. FIG. 3C is a graph illustrating an average of the segments illustrated in FIG. 3B.

FIG. 4A illustrates an exemplary average deceleration segment. FIG. 4B illustrates an exemplary average acceleration segment.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Figure 1:
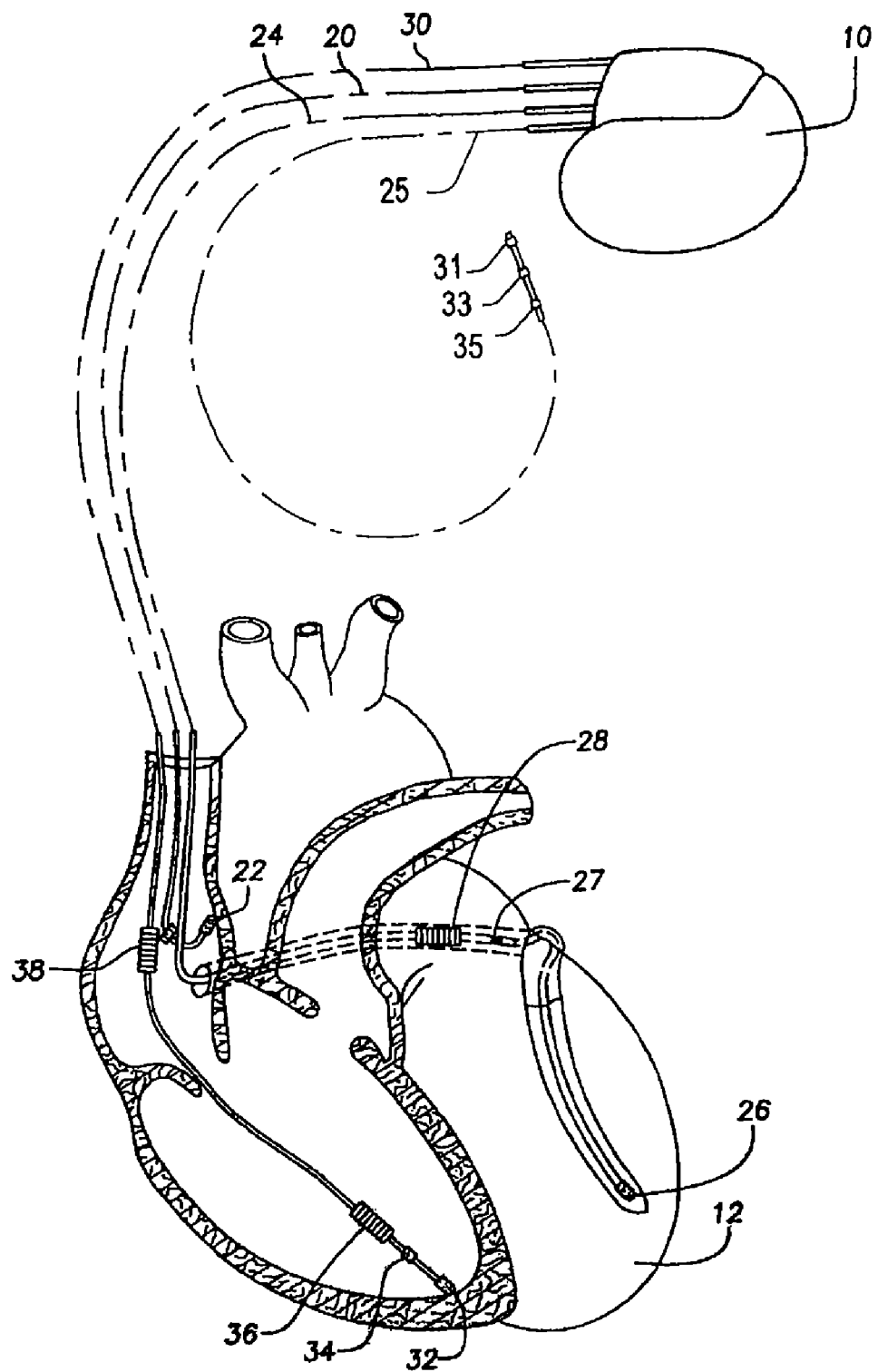
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
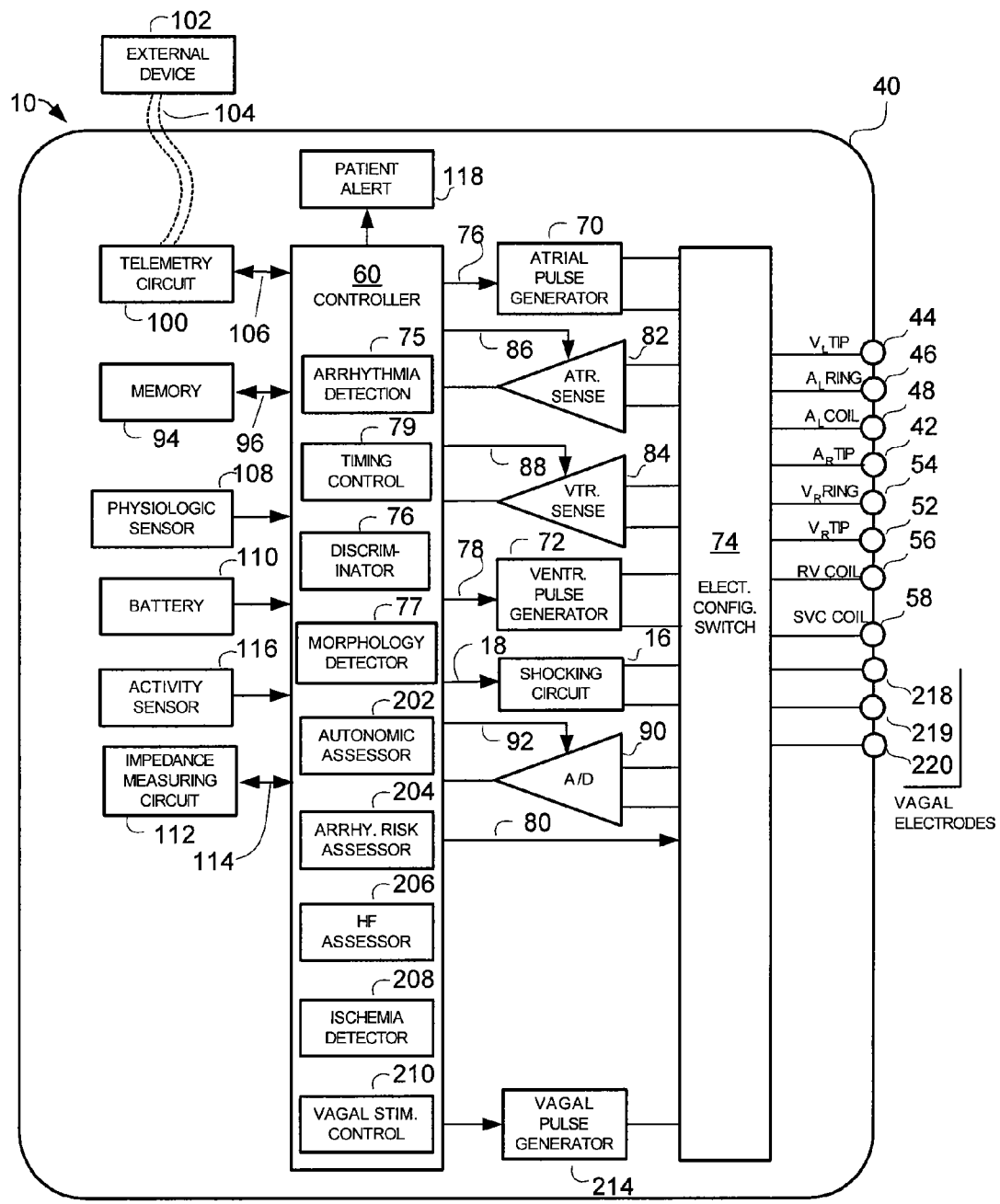
FIG. 2 is a functional block diagram of an exemplary ICD that can provide cardioversion, defibrillation, and pacing stimulation in four chambers of a heart, and performing cardiac and autonomic assessments, in accordance with embodiments of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply is used herein to refer to any implantable cardiac device. FIGS. 1 and 2 illustrate such an environment in which embodiments of the present invention can be used.

Referring first to FIG. 1, an exemplary implantable device 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, implantable device 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, implantable device 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The implantable device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, the implantable device 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of the implantable device 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of the implantable device 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of the implantable device 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses. The implantable device 10 can also include a sympathetic pulse generator (not shown) that is controlled by a sympathetic stimulation controller (within microcontroller 60), to trigger or inhibit delivery of sympathetic stimulation. Such sympathetic stimulation can include, e.g., pulse trains that are delivered via electrodes (e.g., basket electrodes) that are implanted within the right ventricular outflow track, or the pulmonary artery, to stimulate sympathetic ganglia.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the implantable device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, the implantable device 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of the implantable device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of the implantable device 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of the implantable device 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

The implantable device 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within the implantable device 10, it is to be understood that physiologic sensor 108 may also be external to the implantable device 10, yet still be implanted within or carried by the patient. More specifically, sensor 108 can be located inside the implantable device 10, on the surface of the implantable device 10, in a header of the implantable device 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The implantable device 10 may also include a magnet detection circuitry (not shown), coupled to microcontroller 60. It is the purpose of the magnet detection circuitry to detect when a magnet is placed over the implantable device 10. A clinician may use the magnet to perform various test functions of the implantable device 10 and/or to signal microcontroller 60 that the external programmer 102 is in place to receive or transmit data to microcontroller 60 through telemetry circuit 100.

As further shown in FIG. 2, the implantable device 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where the implantable device 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 joules), moderate (about 0.5-10 joules), or high energy (about 11 to 40 joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

The implantable device 10 additionally includes a battery 110, which provides operating power to a load that includes all of the circuits shown in FIG. 2.

In accordance with embodiments of the present invention, the implantable device 10 includes modules 202, 204, 206 and 208 which, as described in more detail below, can respectively assess a patient's autonomic tone, assess a patient's risk of a cardiac arrhythmia, assess a state of heart failure (HF) and detect ischemic events. Other modules not specifically shown in FIG. 2, can be included, as will be appreciated from the description below. Each module can be implemented within the microcontroller 60, as shown in FIG. 2. Thus, such modules can be implemented by software, firmware, or combinations thereof. It is also possible that all, or portions, of modules can be implemented using hardware. Further, it is possible that all or portions of the modules be implemented external to the microcontroller 60. Additionally, as will be appreciated from the description set forth below, because many of the features performed by modules are similar, such modules can be combined.

In an embodiment, one or more of the modules can trigger data acquisition circuit 90 and timing control circuit 79 to sense an EGM signal. The modules can also trigger implantable device 10 to respond appropriately when certain assessments or detections are made, as will be explained in more detail below. Additionally, in conjunction with a telemetry circuit 100, the modules can be configured to deliver status information to an external device 102 through an established communication link 104. Such modules may also trigger a patient or physician alert, as will be described below. For example, a patient alert 118, which produces a vibratory or auditory alert, may be triggered.

Phase Rectified Signal Averaging (PRSA)

It has been recently demonstrated that Phase Rectified Signal Averaging (PRSA) is superior to techniques that use SDNN and left ventricular ejection fraction (LVEF) for prediction of late mortality after a patient has experienced an acute myocardial infarction (AMI). To support such findings, Holter recordings were obtained for a training sample of patients that survived an AMI. PRSA was then used to analyze the Holter recordings of the patients, to thereby predict which patients would experience late mortality (i.e., not survive) and which patient's would not experience later mortality (i.e., survive). Without elaboration, one such publication suggested that the PRSA method may also be proposed for a variety of other applications.

The inventors of the present invention believe that PRSA techniques can be used by implantable cardiac devices, to independently monitor levels of parasympathetic tone and sympathetic tone, even in patients that have never experienced an AMI. From such levels of parasympathetic tone and sympathetic tone, an autonomic nervous system index (ANSi) can be derived. In specific embodiments of the present invention, the monitored levels of parasympathetic tone and sympathetic tone, and/or the ANSi, can be used to detect a heightened risk for a cardiac arrhythmia. In other embodiments, these metrics can be used to track the state of heart failure. In further embodiments, these metrics can be used to detect ischemia, including myocardial ischemia. In other embodiments, these metrics can be used to detect apnea. In further embodiments, these metrics can be used to increase defibrillation success. In still other embodiments, these metrics are used to detect hypoglycemia. In other embodiments, these metrics can be used for early detection of diabetic neuropathy. Each of these embodiments are discussed in additional detail below.

For completeness, prior to discussing the specific embodiments just set forth above, PRSA techniques will first be generally described. The first step in this technique is to obtain a cardiac signal from a patient of interest. Prior publications teach using an ambulatory Holter recording device to obtain an ECG signal from a patient that has survived an acute myocardial infarction (AMI), and then analyzing the recorded ECG signal for the purpose predicting late mortality after the AMI. In contrast, in accordance with embodiments of the present invention, rather than obtaining an ECG signal from an ambulatory device, an implantable cardiac device is preferably used to sense a cardiac electrogram (EGM) signal using implanted electrodes that are endocardial (inside the heart), epicardial (on the surface of the heart) and/or subcutaneous (under the skin, but not in contact with the heart). Accordingly, in one embodiment the cardiac electrogram is an intracardiac electrogram (IEGM) signal, but embodiments are not limited thereto. Measures of RR intervals are then obtained for a window of the cardiac signal. An exemplary plot of 100,000 RR intervals is shown in FIG. 3A, with the horizontal axis indicating beat number, and the vertical axis indicating the RR intervals in milliseconds (ms). The next step is to identify each RR interval that is longer than the immediately preceding RR interval as an anchor point. The anchor points are shown as solid black circles in FIG. 3A, with 45,000 anchor points being identified. Then, for each anchor point, a segment (also referred to as a "window") of N consecutive RR intervals is defined, with the segment being generally centered about the anchor point. Thus, if 45,000 anchor points are identified, then 45,000 segments or windows are defined. FIG. 3B shows the first three segments, and the last segment, with each segment including 30 consecutive RR intervals in this example. In each segment or window, the anchor point is numbered "0" on the horizontal axis, with the segment being generally centered about the anchor point. A next step is to average the segments created for the anchor points to produce an average segment, which has been referred to as an average phase-rectified signal. This can be done by lining up all the segments, such that the anchor points are lined up, and then averaging the lined up RR intervals from each segment. In the left most graph of FIG. 3C, the numerous light gray lines are illustrative of the segments that are created for each of the anchor points, and the dark line in the center illustrates the average segment. The right most graph of FIG. 3C is a more focused view of the average segment.

Figure 4A:
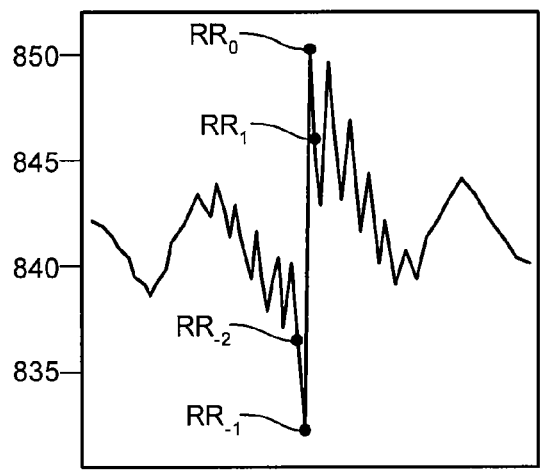
FIGS. 4A and 4B illustrate exemplary average segments.
Figure 4B:
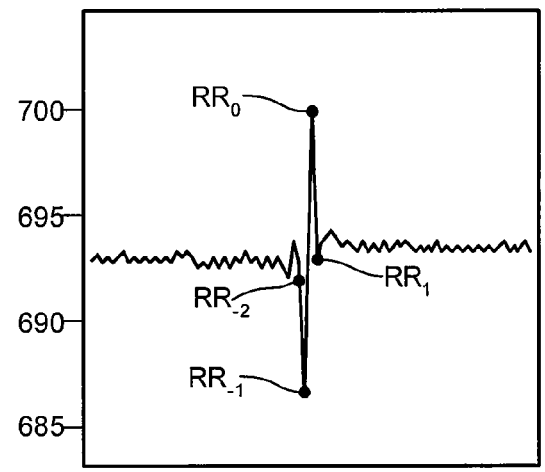

As mentioned above, prior publications have used PRSA based on ambulatory Holter recordings for prediction of late mortality after acute myocardial infarction (AMI). To do this, the PRSA was quantified based on the amplitude of the central wavelet (C) of the average segment, which can be estimated using the equation: $C=(RR_0+RR_1)-(RR_{-1}+RR_{-2})$. The graph of FIG. 4A shows points $RR_0$, $RR_1$, $RR_{-1}$ and $RR_{-2}$ for an exemplary patient that did not experience late mortality after AMI (i.e., for a survivor). The graph of FIG. 4B shows points $RR_0$, $RR_1$, $RR_{-1}$ and $RR_{-2}$ for an exemplary patient that experienced late mortality after AMI (i.e., for a non-survivor). Notice how the amplitude of C is significantly greater for the survivor, than for the non-survivor.

It is the inventors' understanding that prior publications have only explained how PRSA techniques can be used with patients that have experienced an AMI. Additionally, it is the inventors' understanding that prior publications have only applied PRSA techniques to ECG signals that were recorded using ambulatory Holter recording devices. Further, the inventors believe that prior publications have limited the use of PRSA techniques for use in predicting late mortality in survivors of AMI, based on ECG signals that were recorded over a relatively short period of time (e.g., two days).

A unique feature of embodiments of the present invention is that PRSA techniques are not limited to use with patients that have experienced an AMI. Another unique feature of specific embodiments of the present invention is that PRSA is applied to EGM signals that are sensed endocardially, epicardially and/or subcutaneously by an implantable cardiac device. An additional unique feature of specific embodiments of the present invention is that PRSA techniques are repeatedly (e.g., continuously or periodically) used by an implantable device to monitor changes in a patients cardiac and/or autonomic condition. A further unique feature of specific embodiments of the present invention is that PRSA is used for real-time cardiac assessment and feedback. For example, in accordance with specific embodiments of the present invention, levels of parasympathetic tone and sympathetic tone are independently monitored in real time, even in patients that have never experienced an AMI. From such monitored levels of parasympathetic tone and sympathetic tone, an autonomic nervous system index (ANSi) is derived, in accordance with certain embodiments. In specific embodiments of the present invention, the monitored levels of parasympathetic tone and sympathetic tone, and/or the ANSI, are used to detect a heightened risk for a cardiac arrhythmia or sudden cardiac death (SCD). In other embodiments, these metrics are used to track the state of heart failure. In further embodiments, these metrics are used to detect ischemia, including myocardial ischemia. In other embodiments, these metrics are used to detect apnea. In further embodiments, these metrics are used to increase defibrillation success. In still other embodiments, these metrics are used to detect hypoglycemia. In other embodiments, these metrics can be used for early detection of diabetic neuropathy. Each of these embodiments are discussed in additional detail below. Further details of these unique features of the various embodiments of the present invention are discussed below.

Independently Monitoring the Parasympathetic and Sympathetic Nervous Systems

The autonomic nervous system is a distinct system of nerves linked to the central nervous system but not under conscious voluntary control. It is responsible for non-voluntary functions, i.e., the "automatic" regulatory functions like breathing, heartbeat, digestion, etc. The autonomic nervous system is further subdivided into the sympathetic and parasympathetic systems. Similarly, autonomic tone, which is a measure of the autonomic nervous system, can be subdivided into sympathetic tone and parasympathetic tone. Measures of autonomic tone could be used to provide an indication of the progression of a disease state, such as heart failure. For example, an increase in sympathetic tone (and a decrease in parasympathetic tone) is indicative of a worsening heart failure condition. Conversely, a decrease in sympathetic tone (and an increase in parasympathetic tone) is indicative of an improving heart failure condition. As described below, embodiments of the present invention can be used to independently assess a patient's sympathetic and parasympathetic tones, as summarized in the flow diagram of FIG. 5.

Figure 5:
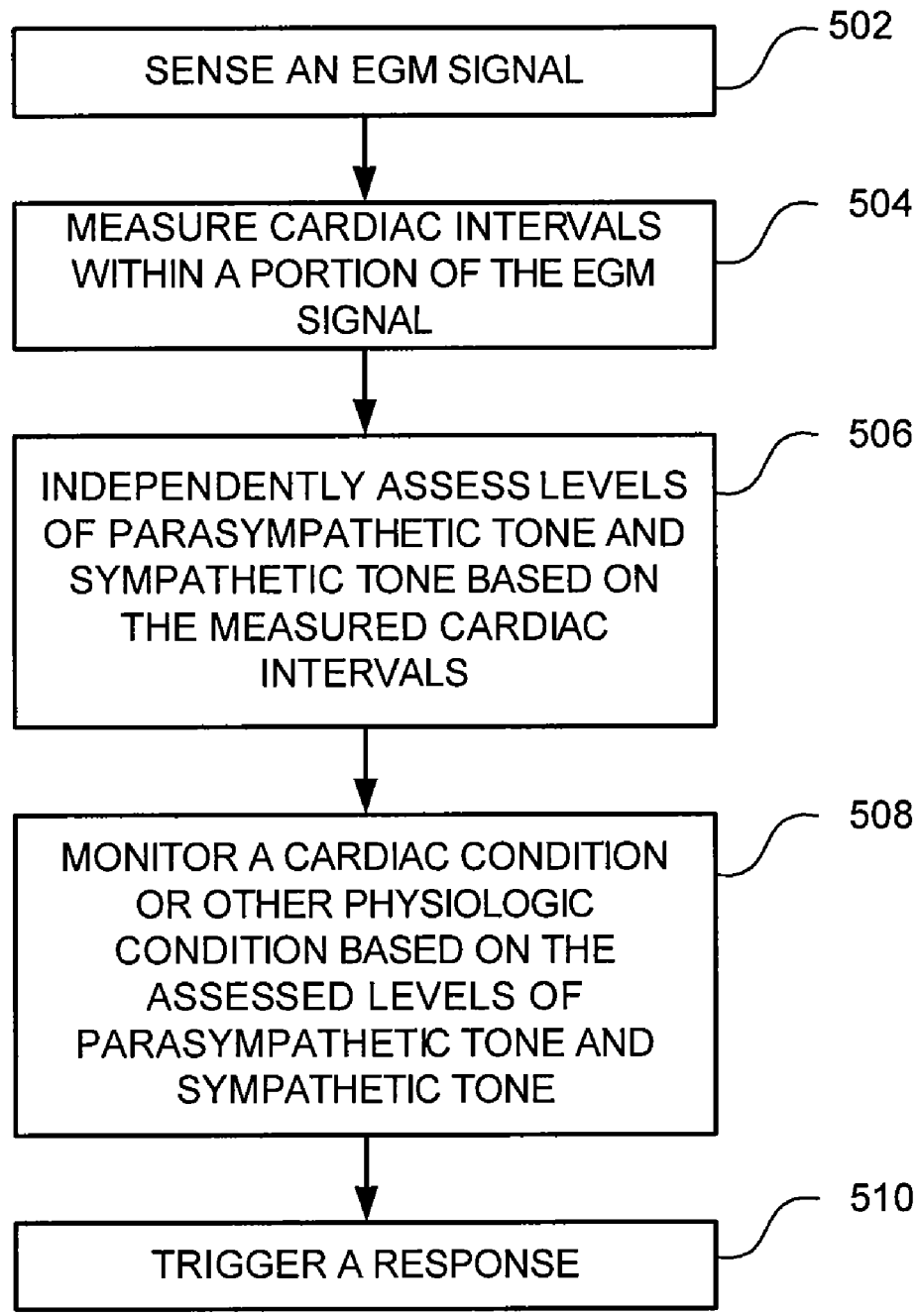
FIG. 5 is a high-level flow diagram that is useful for describing embodiments of the present invention that independently assess a patients' level of parasympathetic tone and sympathetic tone.

In FIG. 5, a flow diagram is shown describing an overview of the operation and novel features that can be implemented in specific embodiments of the device 10. In this flow diagram, and the other flow diagrams described herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of the stimulation device. Those skilled in the art may readily write such a control program based on the flow diagrams and other descriptions presented herein.

Referring to FIG. 5, at a step 502 a cardiac electrogram (EGM) signal is sensed using an implantable device (e.g., a monitor, pacemaker or ICD). At a step 504, cardiac intervals are measured within a portion of the sensed EGM signal. In specific embodiments, step 504 can include detecting cardiac events in the portion of the EGM signal, and then measuring cardiac intervals based on the detected cardiac events. For example, each cardiac cycle of an EGM signal includes a P-wave that is a normally small positive wave caused by the beginning of a heart beat and representing atrial depolarization. Following the P-wave there is a portion which is substantially constant in amplitude. The QRS complex (representing ventricular depolarization) of the EGM then normally occurs after the substantially constant portion, beginning with a Q-wave that is normally a small negative deflection, which is then immediately succeeded by the R-wave that is a rapid positive deflection. Following the R-wave, the QRS complex is completed with an S-wave that is generally characterized by a small positive inflection in the EGM signal. Following the S-wave is a T-wave (representing ventricular repolarization), which is separated from the S-wave by the ST-segment. The cardiac intervals that are measured at step 504 can be, e.g., RR intervals, PP intervals or PR intervals. An exemplary plot of measured RR intervals versus beat numbers is shown in FIG. 3A, which was discussed above.

At a step 506, levels of parasympathetic tone and sympathetic tone are independently assessed based on the measured cardiac intervals. Steps 602-608 of FIG. 6, discussed below, relate to assessing the patient's parasympathetic tone based on measured cardiac intervals, in accordance with a specific embodiment of the present invention. Steps 702-708 of FIG. 7, discussed below, relate to assessing the patient's sympathetic tone based on measured cardiac intervals, in accordance with a specific embodiment of the present invention. Steps 802-804 of FIG. 8, discussed below, relate to assessing the patient's sympathetic tone based on measured cardiac intervals, in accordance with another embodiment of the present invention. Such assessed levels of parasympathetic and sympathetic tone can be used to assess a cardiac condition or other physiologic condition, as indicated at step 508, and to trigger an appropriate response, as indicated at step 510.

Since embodiments of the present invention are intended to be used with a chronically implanted device, each time the device assesses independent levels of parasympathetic and sympathetic tone, the device can store information indicative of the levels so they can be compared with one or more previously assessed levels and/or one or more levels assessed in the future, thereby enabling the device to track changes in the patient's levels of parasympathetic and sympathetic tone. In other words, steps 502-506 can be repeated from time to time (e.g., continually, once a day, once a week or once a month, etc.) so that changes in a patient's levels of parasympathetic and sympathetic tone can be monitored. It is also within the scope of the present invention that such information can be used when determining whether a patient should be upgraded to a device capable of delivering shock therapy, such as an ICD.

The portion of the sensed EGM signal, within which cardiac intervals are measured at steps 504, can be specified by a sliding window. This would be a useful way for using the embodiments of the present invention on a generally continuous basis, to thereby track changes in levels of parasympathetic and sympathetic tone. For example, such a sliding window (and thus, the "portion" of the sensed EGM signal from which measurements are made at step 504), can be a 500 beat long sliding window. The next sliding window can be simply shifted over a single beat, or preferably a more significant distance, such as 50 beats, to avoid almost complete overlap of consecutive sliding windows/portions of the EGM signal that are analyzed. It is also possible that consecutive sliding windows do not overlap at all (e.g., consecutive 500 beat windows can be separated by 50 beats).

Parasympathetic Tone

Figure 6:
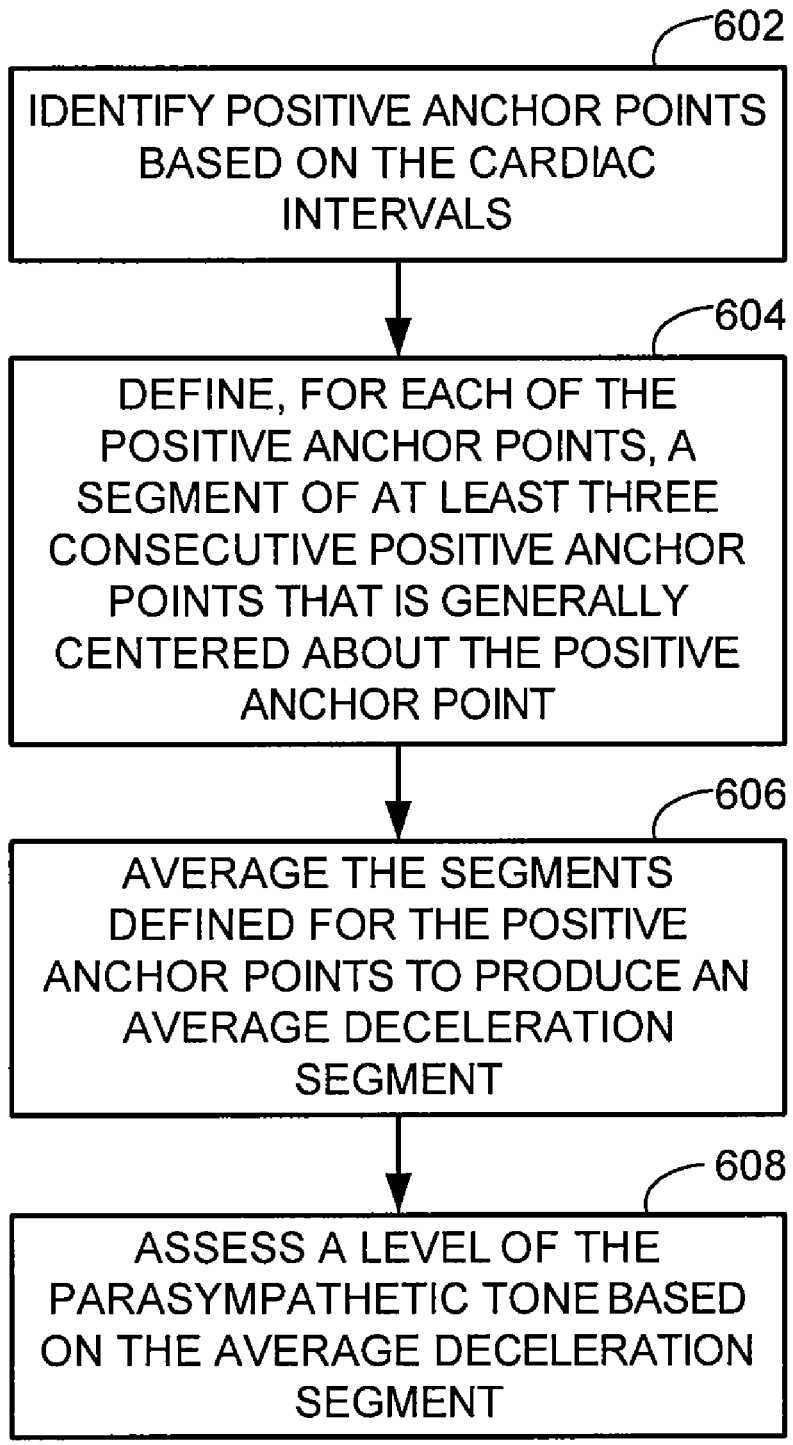
FIG. 6 is a high-level flow diagram that is useful for describing how a level of parasympathetic tone can be determined based on measured cardiac intervals, in accordance with a specific embodiment of the present invention.

FIG. 6 is a high level flow diagram that is used to explain how parasympathetic tone can be assessed at step 506, in accordance with an embodiment. Referring to FIG. 6, at a step 602, each cardiac interval that is longer than the immediately preceding cardiac interval is identified as a positive anchor point. Referring back to FIG. 3A, the solid black circles illustrate exemplary positive anchor points.

At a step 604, a segment (e.g., window) of at least three consecutive cardiac intervals is defined for each identified positive anchor point, where the segment is generally centered about the positive anchor point. For example, FIG. 3B shows the first three segments, and the last segment, that are defined for 45,000 identified positive anchor points, with each segment including 30 consecutive RR intervals. In FIG. 3B, in each segment or window, the positive anchor point is numbered "0" on the horizontal axis, with the segment being generally centered about the positive anchor point. It is noted, however, that the anchor point need not be as centered as shown in FIG. 3B. For example, if each segment includes 10 consecutive RR intervals, the positive anchor point of each segment could be the third RR interval, with two RR intervals prior to the positive anchor point and seven RR intervals after the positive anchor point, within the segment.

Where segments are centered around positive anchor points (indicative of cardiac intervals that are longer than the immediately preceding cardiac interval), the segments may be referred to hereafter as deceleration segments. This is because a lengthening of a cardiac interval (e.g., RR interval) is indicative of a deceleration in heart rate.

At a step 606, the segments defined for the positive anchor points are averaged (e.g., ensemble averaged) to produce an average deceleration segment. An exemplary average deceleration segment is shown in FIG. 3C.

At a step 608, a level of the parasympathetic component of the patient's autonomic nervous system is assessed based on the average deceleration segment. This can be accomplished in various manners, as will now be explained. In accordance with certain embodiments of the present invention, a patient's parasympathetic tone is assessed based on characteristics or metrics of the parasympathetic central wavelet ($C_p$) of the average deceleration segment, where the parasympathetic central wavelet is the wavelet of maximum amplitude of the average deceleration segment. For example, a level of parasympathetic tone can be based on the amplitude of the parasympathetic central wavelet ($C_p$) of the average deceleration segment, which can be estimated using the equation: $C_p = (RR_0 + RR_1) - (RR_{-1} + RR_{-2})$. In other words, the greater the amplitude of the parasympathetic central wavelet, the greater the parasympathetic tone; and the lower the amplitude of the parasympathetic central wavelet, the lower the parasympathetic tone. Thus, referring back to FIGS. 4A and 4B, FIG. 4A would be representative of a greater parasympathetic tone than FIG. 4B. An alternative equation that can be used to characterize the parasympathetic central wavelet is $(RR_0 + RR_1)/2 - (RR_{-1} + RR_{-2})/2$. In still another embodiment, the parasympathetic central wavelet can be simply characterized by $RR_0$. Where the cardiac intervals are PP intervals or PR intervals, instead of RR intervals, measures of PP intervals or PR intervals can be substituted in the equations discussed above.

The above description provides just a few example metrics of the parasympathetic central wavelet of the average deceleration segment that can be measured. Based on the description herein, one of ordinary skill in the art will appreciate that uses of other metrics are also within the scope of the present invention.

In still another embodiment, a forward time constant of the average deceleration segment can be determined, which is representative of the amount of time it takes the average deceleration segment to go from its peak to a baseline value. Other definitions of time constant may also be used. For example, the time constant may be defined as the time it takes the average deceleration segment to go from its peak to 37% of the peak value. For example, referring to FIGS. 4A and 4B, it can be appreciated that the forward time constant for the average deceleration segment of FIG. 4A is significantly greater than the forward time constant for the average deceleration segment of 4B. Similarly, a backward time constant of the average deceleration segment can be determined, which is representative of the amount of time that it takes for the average deceleration segment to go from a baseline value to its peak. Referring again to FIGS. 4A and 4B, it can be appreciated that the backward time constant for the average deceleration segment of FIG. 4A is significantly greater than the backward time constant for the average deceleration segment of 4B. In these embodiments, increases in forward and/or backward time constant are indicative of increases in the patient's level of parasympathetic tone, and decreases in the forward and/or backward time constant are indicative of decreases in the patient's level of parasympathetic tone.

In still another embodiment, the forward slope of a best fit line can be determined, which is representative of the amount of time it takes the average deceleration segment to go from a baseline value to its peak, or a backward slope can be determined, which is representative of the amount of time it takes the average deceleration segment to go from its peak to a baseline value. For example, at least 3 (and preferably at least 5) points can be used to specify a best fit line, from which a forward and/or backward slope can be determined. For example, referring to FIGS. 4A and 4B, it can be appreciated that the magnitudes of the forward and backward slopes (i.e., absolute values of the slopes) for the average deceleration segment of FIG. 4A are less than the magnitudes of the forward and backward the slopes of the average deceleration segment of 4B. In these embodiments, increases in forward and/or backward slope may be indicative of decreases the patient's parasympathetic tone, and decreases in the forward and/or backward slopes may be indicative of increases in the patient's parasympathetic tone.

In each of the above embodiments, the measurements of the parasympathetic central wavelet, time constant or slope can be used raw, or they can be normalized before they are used. Such normalization can be achieved, e.g., by dividing a raw value by a normalization value. The normalization value can be specific to the patient, and determined and set, e.g., at the time the cardiac device is implanted. Alternatively, the normalization value can be set based on a broad patient population. A benefit of normalizing measurements is that if measurements are to be compared to one or more threshold, then the thresholds can be defined for a patient population (as opposed to having to specify thresholds for each patient). Another benefit of normalizing measurements of parasympathetic tone is that they can be compared to and/or combined with normalized measures of sympathetic tone, as will be described below.

In one embodiment, measurements are normalized based on their circadian max/min values over a certain period of time (e.g., 24 hours). In normal circumstances, the level of parasympathetic tone will be highest at night time and lowest in the early morning hours. Maximum and minimum values can be determined for each parameter (e.g., the parasympathetic central wavelet, time constant and/or slope) and can be stored and averaged over several days during normal patient conditions in order to produce normalization values. Measurements can alternatively be normalized using a fixed value (e.g., a programmable value) based on averages in a population of healthy individuals. In a specific embodiment, measurements are normalized such that each measurement is between zero and one, with zero indicating the lowest level, and one indicating the highest level, for each parameter.

Each of the above metrics that are determined from an average deceleration segment (before or after normalization) can be compared to one or more threshold to determine a level of parasympathetic tone. For example, if a single threshold is used, then a level of parasympathetic tone can be classified as high if the metric is above the threshold, or low if the metric is below the threshold. If two thresholds are used, then the level of parasympathetic tone can be classified as high, medium or low. Of course, more thresholds can be used if the desire is to provide more levels of parasympathetic tone.

Figure 8A:
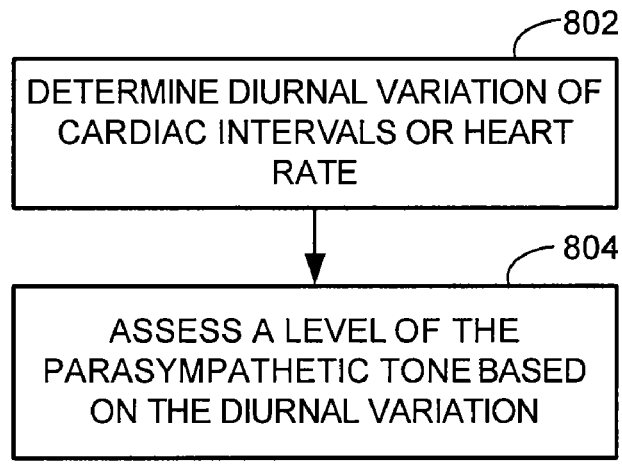
FIG. 8A is a high-level flow diagram that is useful for describing how a level of parasympathetic tone can be determined, in accordance with alternative embodiments of the present invention.

Alternatively, to compute parasympathetic tone, a diurnal variation can be determined based on the cardiac intervals measured at step 504, and the level of sympathetic tone can be based on the extent of diurnal variation, as shown in steps 802 and 804 of FIG. 8A. In such an embodiment, a low diurnal variation is indicative of a low parasympathetic tone, and a high diurnal variation is indicative of a high parasympathetic tone. The diurnal variation can be a measure of change in cardiac intervals, or heart rate, over the course of a day. Measures of diurnal variation can be compared to one or more threshold to classify the patient's sympathetic tone as one of two or more levels.

Sympathetic Tone

Figure 7:
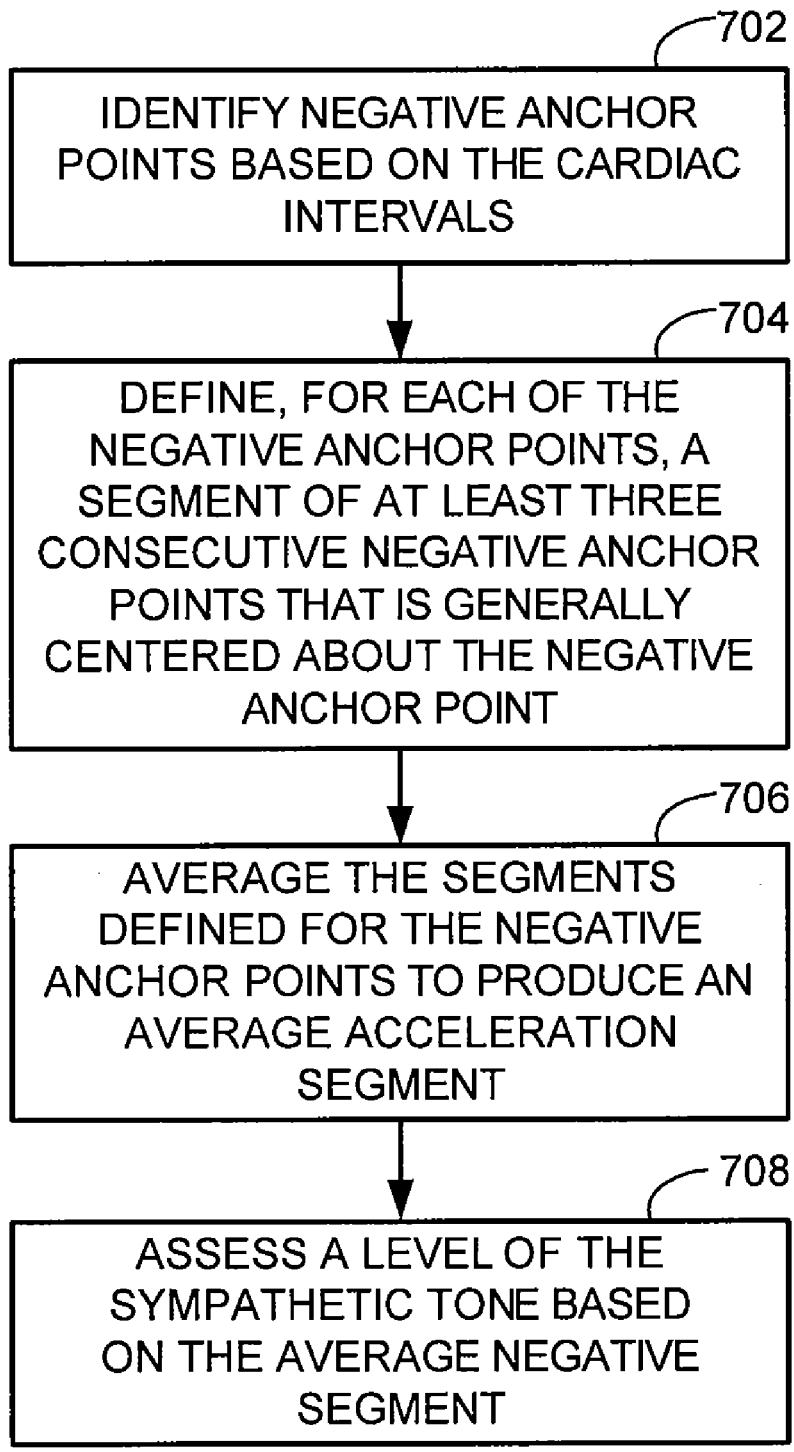
FIG. 7 is a high-level flow diagram that is useful for describing how a level of sympathetic tone can be determined based on measured cardiac intervals, in accordance with a specific embodiment of the present invention.

FIG. 7 is a high level flow diagram that is used to explain how sympathetic tone can be assessed at step 506, in accordance with an embodiment. The steps of FIG. 7 can be performed prior to, after, or at the same time as the steps of FIG. 6. Referring to FIG. 7, at a step 702, negative anchor points are identified as each cardiac interval that is shorter than the immediately preceding cardiac interval.

At a step 704, a segment (e.g., window) of at least three consecutive cardiac intervals is defined for each identified negative anchor point, where the segment is generally centered about the negative anchor point. Where segments are centered around negative anchor points (indicative of cardiac intervals that are shorter than the immediately preceding cardiac interval), the segments may be referred to hereafter as acceleration segments. This is because a shortening of a cardiac interval (e.g., RR interval) is indicative of an acceleration in heart rate. Preferably the number of cardiac intervals in each segment in step 704 is the same as the number of intervals in each segment in step 604.

At a step 706, the segments defined for the negative anchor points are averaged (e.g., ensemble averaged) to produce an average acceleration segment. Step 706 is similar to step 606 discussed above, except that in step 706 segments that are defined for negative anchor points (as opposed to positive anchor points) are being averaged.

At a step 708, a level of the sympathetic component of the patient's autonomic nervous system is assessed based on the average acceleration segment. This can be accomplished in various manners, as will now be explained. In accordance with certain embodiments of the present invention, a patient's sympathetic tone is assessed based on characteristics or metrics of the sympathetic central wavelet ($C_s$) of the average acceleration segment, where the sympathetic central wavelet is the wavelet of maximum amplitude of the average acceleration segment. For example, a level of sympathetic tone can be based on the amplitude of the sympathetic central wavelet ($C_s$) of the average acceleration segment, which can be estimated using the equation: $C_s = (RR_0 + RR_1) - (RR_{-1} + RR_{-2})$. In other words, the greater the amplitude of the sympathetic central wavelet, the greater the sympathetic tone; and the lower the amplitude of the sympathetic central wavelet, the lower the sympathetic tone. An alternative equation that can be used to characterize the sympathetic central wavelet is $(RR_0 + RR_1)/2 - (RR_{-1} + RR_{-2})/2$. In still another embodiment, the sympathetic central wavelet can be simply characterized by $RR_0$. Where the cardiac intervals are PP intervals or PR intervals, instead of RR intervals, measures of PP intervals or PR intervals can be substituted in the equations discussed above.

Additionally or alternatively, a forward time constant and/or a backward time constant can be determined for the average acceleration segment, in a similar manner as was discussed above. The time constant (or a normalized version thereof) can then be compared to one or more threshold to specify a level of sympathetic tone. In this embodiment, an increase in a forward and/or backward time constant can be recognized as being indicative of a decrease in sympathetic tone. Conversely, a decrease in a forward and/or backward time constant can be recognized as being indicative of an increase in sympathetic tone.

Additionally or alternatively, a forward slope and/or a backward slope can be determined for the average acceleration segment, in a similar manner as was discussed above. The slope (or a normalized version thereof) can then be compared to one or more threshold to specify a level of sympathetic tone. In this embodiment, an increase in the magnitude of forward and/or backward slope can be recognized as being indicative of an increase in sympathetic tone. Conversely, a decrease in the magnitude of forward and/or backward slope is recognized as being indicative of a decrease in sympathetic tone.

In one embodiment, measurements are normalized based on their circadian max/min values over a certain period of time (e.g., 24 hours). In normal circumstances, the level of sympathetic tone will be lowest at night time and highest in the early morning hours. Maximum and minimum values can be determined for each parameter (e.g., the sympathetic central wavelet, time constant and/or slope) and can be stored and averaged for over several days during normal patient conditions in order to produce a normalization values. Measurements can alternatively be normalized using a fixed value (e.g., programmable value) based on averages in a population of healthy individuals. In a specific embodiment, measurements are normalized such that each measurement is between zero and one, with zero indicating the lowest level, and one indicating the highest level, for each parameter.

Each of the above metrics that are determined from an average acceleration segment (before or after normalization) can be compared to one or more threshold to determine a level of sympathetic tone. For example, if a single threshold is used, then a level of sympathetic tone can be classified as high if the metric is above the threshold, or low if the metric is below the threshold. If two thresholds are used, then the level of sympathetic tone can be classified as high, medium or low. Of course, more thresholds can be used if the desire is to provide more levels of sympathetic tone.

Figure 8B:
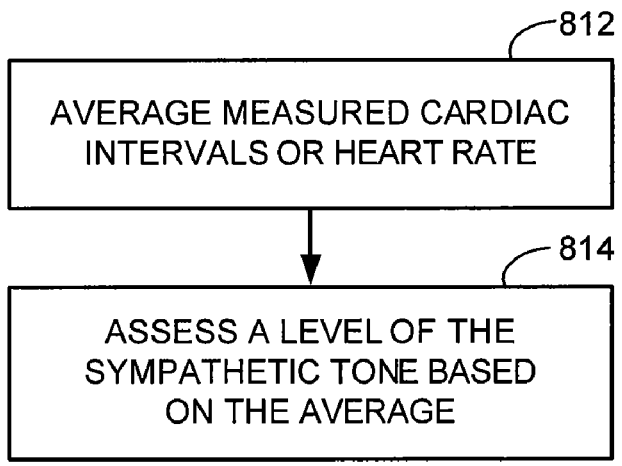
FIG. 8B is a high-level flow diagram that is useful for describing how a level of sympathetic tone can be determined, in accordance with alternative embodiments of the present invention.

Alternatively, to compute sympathetic tone, the cardiac intervals measured at step 504 (or a heart rate determined based on the cardiac intervals) can be averaged, and the level of sympathetic tone can be based on the average, as shown in steps 812 and 814 of FIG. 8B. In such an embodiment, a low average heart rate (or long average cardiac interval) is indicative of a low sympathetic tone, and a high average heart rate (or short average cardiac interval) is indicative of a high sympathetic tone. The average heart rate (or cardiac interval) can be, e.g., an average of 24 hours, a day-time average, or an average of a period of time during the day.

Monitoring Conditions and Responding Thereto

Referring back to FIG. 5, as mentioned above, at step 508 a cardiac condition or other physiologic condition can be monitored based on the independently assessed levels of parasympathetic tone and sympathetic tone, and/or based on a combined sympathetic/parasympathetic index, referred to hereafter as an autonomic nervous system index (ANSi). Given that the sympathetic and parasympathetic systems exert opposite effects on the heart, similar to two opposite forces applied to a rope at its two ends, the combined net effect on heart (rate) can be assumed to be the addition of two opposite force vectors (i.e., Force=sympathetic level–parasympathetic level). Since the methods for calculating a patient's sympathetic level and parasympathetic level as described above can produce the two parameters as a function of time through use of a sliding window (of N seconds), the net force, F, can also be produced as a function of time. Double integration of the function F will produce a function that is proportional to the resulting combined sympathetic and parasympathetic net effect on the heart (or in the rope analogy, the resulting relative displacement of the rope), or the, ANSi.

In certain embodiments, step 508 includes detecting a heightened risk for a cardiac arrhythmia and/or to determining a risk of sudden cardiac death (SCD). In other embodiments, step 508 includes tracking the state of heart failure. In further embodiments, step 508 includes detecting ischemia, including myocardial ischemic events. In other embodiments, step 508 including detecting apnea. In further embodiments, step 508 includes detecting hypoglycemia. In other embodiments, step 508 includes early detection of diabetic neuropathy. Each of these embodiments are discussed in additional detail below.

At a step 510, one or more response can be triggered based on the monitoring performed at step 508. For example, step 510 can include storing information used to assess levels of parasympathetic and sympathetic tone for later retrieval and/or transmission to a physician or other clinician. Additionally, or alternatively, step 510 can include storing assessed levels of parasympathetic and sympathetic tone, and/or ANSi. Accordingly, step 510 can include storing metrics of the average acceleration and deceleration segments (produced at steps 606 and 706), such as data points of the central wavelets ($C_p$ and $C_s$), amplitudes of the central wavelets, forward time constants, backward time constants, forward slopes, backward slopes, etc. It is also possible that data representative of the actual average acceleration and deceleration segments are saved. Such information can be displayed with previously determined information, from say a month ago, and compared to see improvement or worsening of the certain conditions. Such information can be continually, or from time to time, automatically uploaded to an external device (e.g., 102). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

In certain embodiments, a patient is alerted when appropriate, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform the patient that he should rest, or if the patient is operating some type of dangerous machinery (e.g., a car), that the patient should stop what they are doing.

Additionally or alternatively, the patient can be instructed to take medication when alerted. In still another embodiment, a physician or other person (e.g., a caregiver, guardian or relative of the patient) is alerted whenever appropriate.

In further embodiments, an appropriate therapy can be triggered in response to specific assessments. One type of therapy would be for an implanted device (e.g., device 10) to stimulate the vagal nerve, in an attempt to slow down the heart rate and increase parasympathetic (vagal) tone, which is known to be generally cardioprotective. In another embodiment, the implanted device, if appropriately equipped, can deliver an appropriate drug therapy. In a further embodiment, an implanted device can deliver sympathetic stimulation, e.g., when a determined level of sympathetic tone is below a threshold and/or when a determined level of parasympathetic tone is more than a threshold amount greater than a determined level of sympathetic tone. One of ordinary skill in the art would appreciate from the description that other types of therapies can be triggered.

As mentioned above, in certain embodiments, measures of parasympathetic tone and sympathetic tone, and/or a combined measure (e.g., ANSi) are monitored (e.g., on a beat to beat basis), to thereby monitor a patient's risk for cardiac arrhythmia at step 508. A state of heightened risk for cardiac arrhythmia and/or risk of sudden cardiac death (SCD) can be detected when there is a trend of increase in normalized sympathetic level, with or without a decrease in normalized parasympathetic level. A state of heightened risk for cardiac arrhythmia and/or risk of SCD can also be detected when there is an absence of upsurge in normalized parasympathetic level following a hypotensive stimulus such as an intrinsic premature ventricular contraction (PVC), an intrinsic premature atrial contraction (PAC), an induced (paced) PVC, an induced PAC, or a simulated PVC (by way of vagal stimulation). Additional details of how to simulate a PVC, by way of vagal stimulation, are described in U.S. patent application Ser. No. 10/861,747, entitled "System and Method for Using Vagal Stimulation to Assess Autonomic Tone and Risk of Sudden Cardiac Death in an Implantable Cardiac Device," filed Jun. 4, 2004 and U.S. patent application Ser. No. 11/061,008, entitled "Systems and Method for Detecting Ischemic Events", filed Feb. 17, 2005, each of which is incorporated herein by reference.

An increased sympathetic tone can be predictive of VT storm which may be preventable by sympathetic blockade though pacing or other approaches. In accordance with an embodiment, sudden abolishment of parasympathetic upsurge following hypotensive stimuli can be considered a predictor of an imminent arrhythmia. For increased specificity, the algorithm can be tied to another algorithm that evaluates the electrical stability (e.g., electrical alternans) of the heart. The algorithm that evaluates electrical stability can do so, e.g., by monitoring for electrical alternans. In this setting, absence of parasympathetic reflex following PVC in presence of heightened electrical instability can be used as a predictor of an impending arrhythmia.

One or more response can be triggered (at step 510) based on the assessed risk for cardiac arrhythmia. In accordance with an embodiment of the present invention, this can involve storing information (examples of which were discussed above) related to the heightened risk for cardiac arrhythmia for later retrieval and/or transmission to a physician or other clinician. In an embodiment, a patient is alerted when a heightened risk for an arrhythmia warrants an alert, thereby allowing the patient to respond appropriately. Example types of alerts were discussed above. Additionally or alternatively, the patient can be instructed to take medication when alerted. In still another embodiment, a physician or other person (e.g., a caregiver, guardian or relative of the patient) can be alerted whenever a heightened risk for an arrhythmia is detected. In further embodiments, a therapy can be triggered in response to assessing a heightened risk for an arrhythmia. One type of therapy would be for an implanted device (e.g., device 10) to stimulate the vagal nerve, in an attempt to slow down the heart rate and increase vagal tone, which is known to be generally cardioprotective. In another embodiment, the implanted device, if appropriately equipped, can deliver an appropriate drug therapy. One of ordinary skill in the art would appreciate from the above description that other types of therapies can be triggered. Another appropriate response, if the patient is at imminent risk of an arrhythmia, is to start charging the capacitor(s) of an ICD, just in case there is a need to deliver shock therapy to the patient. In still another embodiment, anti-arrhythmia therapy (e.g., anti-arrhythmia pacing) can be delivered if it is determined that the patient is at risk of an imminent arrhythmia.

These are just a few examples of the types of responses that can be performed upon assessing a heightened risk for an arrhythmia. One of ordinary skill in the art would understand from the above description that other responses are also possible, while still being within the spirit and scope of the present invention.

It is also within the scope of the present invention that the assessed levels of parasympathetic tone and sympathetic tone, and/or the assessed risk of an arrhythmia, can be used when determining whether a patient should be upgraded to a device capable of delivering shock therapy, such as an ICD.

In another embodiment, monitoring the long term trend in autonomic tone (daily/weekly trends, etc.) can be used to track the state of heart failure. It can also be used to track the efficacy of medication and assist with medication selection and/or dosing. Long-term changes in autonomic tone of a patient with a trend of increasing sympathetic tone can be representative of HF progression and may be communicated to the patient, physician, or other third party. Short-term and significant changes in autonomic tone in the polarity of increasing sympathetic tone may be predictive or representative of imminent HF exacerbation, which may be communicated to the patient, physician, or other third party.

As mentioned above, in certain embodiments, measures of parasympathetic tone and sympathetic tone, and/or a combined measure (e.g., ANSi) are monitored (e.g., on a beat to beat basis), to thereby monitor for myocardial ischemic episodes at step 508. Myocardial ischemia is an intermediate condition in coronary artery disease during which the heart tissue is slowly or suddenly starved of oxygen and other nutrients. Eventually, the affected heart tissue will die. When blood flow is completely blocked to the heart, ischemia can lead to a myocardial infarction (also know as a "heart attack"). According to the American Heart Association, up to four million Americans may have silent ischemia and be at high risk of having a myocardial infarction with no warning. In addition, the American Heart Association estimates that nearly seven million Americans have angina pectoris, usually called angina. Therefore, by monitoring ischemia and alerting patients to seek immediate medical attention when necessary, regardless of whether the ischemia is associated with symptoms or not has relevance to patient outcomes and survival. Many ischemia monitoring algorithms detect episodes of ischemia by detecting an acute voltage shift in the ST-segment of an intracardiac electrocardiogram (ECG). It would be useful if other techniques could be used to supplant or surrogate ischemia monitoring algorithms that rely ST-segment shift analysis.

In accordance with specific embodiments of the present invention, a myocardial ischemic episode can be detected when there is a transient (i.e., temporary) increase in sympathetic tone. In other words, transient increases in sympathetic tone can be used as a marker for ischemic episodes, in accordance with embodiments of the present invention. In accordance with an embodiment of the present invention, this can be accomplished by detecting temporary decreases in a metric (e.g., amplitude) of the central wavelet of an average deceleration segment, or detecting temporary increases in a metric (e.g., amplitude) of the central wavelet of an average acceleration segment. Additionally, or alternatively, myocardial ischemic events can be detected by detecting temporary decreases in the forward and/or backward time constant of an average acceleration segment. Additionally, or alternatively, myocardial ischemic events can be detected by detecting temporary increases in the forward and/or backward slope of an average acceleration segment. Such temporary decreases or increases can be detected, e.g., by comparing a most recently determined metric (e.g., amplitude) of a sympathetic central wavelet, time constant and/or slope to a corresponding baseline, with the baseline being representative of an average acceleration segment when the patient is not experiencing a myocardial ischemic event. In a specific embodiment, a myocardial ischemic event is identified (at step 508) when the measured metric of the average acceleration segment deviates from the baseline by more than a threshold. The baseline can be defined when the implantable device is implanted, or the baseline can simply be a running average of all average acceleration segments, which would essentially average out those segments corresponding to an ischemic event. Other ways for determining the baseline are also within the scope of the present invention. Additionally, other ways for detecting temporary changes in a metric (e.g., amplitude) of a sympathetic central wavelet, temporary decreases in a time constant and/or temporary increases in a slope of the average acceleration segment are within the scope of the present invention.

At step 510, one or more response can be triggered in response to detecting an ischemic event. A myocardial infarction (i.e., a heart attack) is always preceded by a myocardial ischemic event. Thus, the detection of a myocardial ischemic event may be indicative of an imminent myocardial infarction. Accordingly, in an embodiment, a patient is alerted when a myocardial ischemic event is detected, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a myocardial ischemic event is detected.

In further embodiments, a myocardial ischemia therapy can be triggered in response to detecting an ischemic event. One type of therapy would be for an implanted device (e.g., device 10) to stimulate the vagal nerve, in an attempt to slow down the heart rate to decrease the metabolic demand. In another embodiment, the implanted device, if appropriately equipped, can deliver an appropriate drug therapy. One of ordinary skill in the art would appreciate from the above description that other types of therapies can be triggered.

These are just a few examples of the types of responses that can be performed upon detection of a myocardial ischemic event. One of ordinary skill in the art would understand from the above description that other responses are also possible, while still being within the spirit and scope of the present invention.

Figure 9:
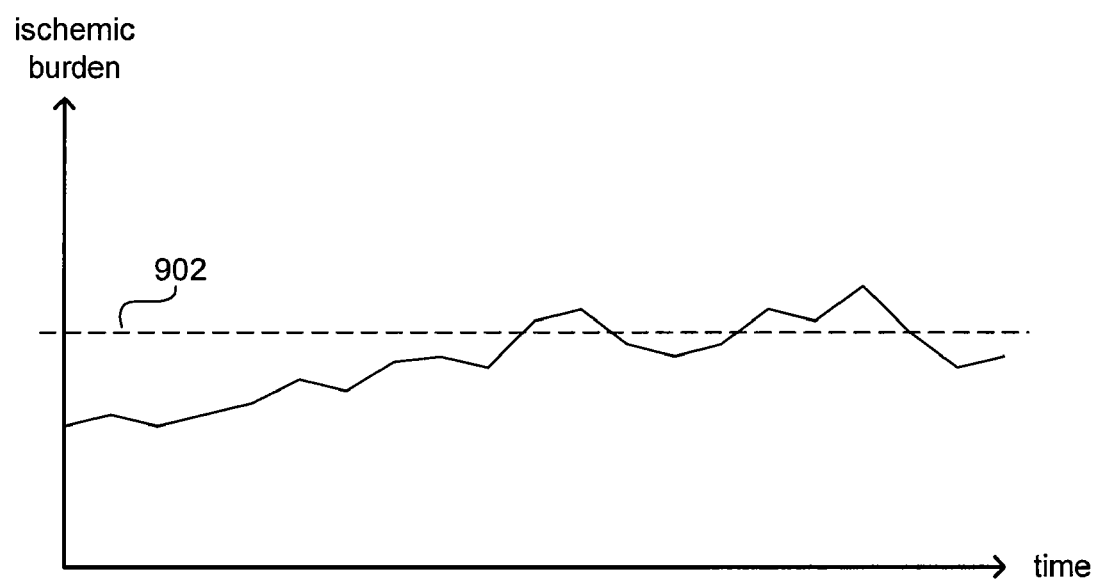
FIG. 9 is an exemplary graph of ischemic burden that can be created using specific embodiments of the present invention.

In accordance with an embodiment of the present invention, ischemic burden can be monitored by determining a number of ischemic events that occur during each predetermined period of time (e.g., 24 hours). By tracking ischemic burden in this manner, there can be a determination of whether ischemic burden has increased or decreased over time. Additionally, one or more ischemic burden threshold can be defined, so that one of the above responses can be triggered in response to a specific ischemic burden threshold being crossed. FIG. 9 illustrates an exemplary graph of ischemic burden over time, with dashed line 902 representing a burden threshold. It is also within the scope of the present invention that ischemic burden, determined using embodiments of the present invention, can be used when determining whether a patient should be upgraded to a device capable of delivering shock therapy, such as an ICD.

For better sensitivity and/or specificity, one of the above mentioned embodiments for detecting ischemia can be tied to other markers indicative of such ischemia, such as an IEGM based algorithm that detects deviations in the ST segment as a marker for ischemia. In this setting, information on timing, duration, and frequency of ischemia episodes can be stored to compute the ischemic burden of patients or communicated to the patient, physician, or other third party.

In another embodiment, increase in sympathetic tone can be used to detect apnea. For example, apnea episodes can be detected during evening hours by detecting transient short surges in sympathetic activity. For increased specificity, respiration information derived by another algorithm based on IEGM or other means (e.g., photoplethysmography or dynamic impedance) can be tied to this algorithm. Upon detection of apnea episodes, the device could start pacing or other stimulation therapies, or alert the patient/physician to consider therapy.

When incorporated in an ICD, the beat to beat information on parasympathetic and sympathetic tone can be used to increase defibrillation success. For example, it has been shown that vagal stimulation during VF lowers the defibrillation threshold (DFT). As such, when inadequate levels of parasympathetic tone are detected immediately prior to VF or during the first few seconds of VF, the algorithm can be set to use a higher energy shock for defibrillation. The reverse can also be used to increase device's longevity. In other words, depending on the detected level of parasympathetic tone immediately before and after VF onset, the required defibrillation energy can be lowered or increased from the programmed value.

In another embodiment, an upsurge in sympathetic tone can be used detect hypoglycemia. To increase the sensitivity and/or specificity of hypoglycemia detection, the increase in sympathetic tone may be used in conjunction with other means of hypoglycemia detection (e.g., EGM morphology changes). The device can be set to trigger therapy or simply store timing and duration information on hypoglycemic periods to calculate hypoglycemic burden for a given period of time, for example, three months.

Early detection of diabetic autonomic neuropathy can also be achieved by monitoring the autonomic tone. Specifically, a gradual decrease in both parasympathetic and sympathetic tone with little or no circadian variation can be an early detector of diabetic autonomic neuropathy and may be used to take a more aggressive approach for diabetes management for the patient or other appropriate therapy. More specifically, it is believed that both parasympathetic tone and sympathetic tone will be blunted as a patient develops diabetic neuropathy. Accordingly, embodiments of the present invention described above can be used to independently monitor levels of both parasympathetic tone and sympathetic tone to detect potential development of diabetic neuropathy.

In accordance with specific embodiments of the present invention, the above mentioned thresholds can be determined for a specific patient, based on previous tests preformed on the patient. Alternatively, thresholds can be defined based on a population, such that the thresholds are defined on a population basis, as opposed to being specific for a patient. More generally, training sets can be used to assess which levels of parasympathetic and sympathetic tone are indicative of which condition. A training set can be based on a population of patients whose cardiovascular autonomic status (including parasympathetic tone and sympathetic tone) is assessed based on "gold standard" cardiovascular autonomic reflex tests that rely on heart rate and blood pressure changes to certain stimuli. Typically autonomic status is quantified based on evaluation both of respiratory sinus arrhythmia during normal and paced breathing. Additionally, assessment of heart rate and blood pressure changes during Valsalva maneuver, tilting, and isometric work under standardized environmental conditions gives further quantification of the autonomic status (Piha 1988, 1993, Ewing 1992, Wieling & Karemaker 1999). Changes in heart rate are a metric of parasympathetic tone levels while blood pressure changes provide an indication of the levels of sympathetic tone. Once these "gold standard" levels of parasympathetic and sympathetic indices have been quantified then the measurement feature may be used as features that relate to the autonomic tone. For example, each subject in the training set may be classified according to their parasympathetic level and sympathetic level. The patient may be classified according to where they land in a normal distribution. For instance, the subject may be classified in the top $90^{th}$ percentile parasympathetic and in the lower $20^{th}$ percentile sympathetic. Note, that because levels of parasympathetic tone and sympathetic tone are determined independently, they may not (and likely will not) add up to 100%. Of course, measures other than percentages can be used, as was suggested above.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Also, it is noted that the term "base on", as used herein, means based at least in part on, unless otherwise specified.

Thus, the breadth and scope of the present invention should not be limited by any of the above-described exemplary embodiments, but should be defined only in accordance with the following claims and their equivalents.

What is claimed is:

1. For use with an implantable device, a method for independently monitoring levels of parasympathetic and sympathetic tone of a patient, comprising:

(a) sensing a cardiac electrogram (EGM) signal using implanted electrodes;

(b) measuring cardiac intervals within a portion of the sensed EGM signal; and (c) independently assessing levels of parasympathetic tone and sympathetic tone based on the measured cardiac intervals, wherein step (c) comprises:

(c.1) assessing the level of parasympathetic tone in one of the following manners:

(c.1.i) determining the patient's diurnal variation of cardiac intervals based on the measured cardiac intervals, wherein diurnal variation of cardiac intervals is a measurement of change in cardiac intervals over the course of a day, and assessing the level of parasympathetic tone based on the diurnal variation of cardiac intervals;

(c.1.ii) determining the patient's diurnal variation of heart rate based on the measured cardiac intervals, wherein diurnal variation of heart rate is a measurement of change in heart rate over the course of a day, and assessing the level of parasympathetic tone based on the diurnal variation of heart rate; and (c.1.iii) identifying each said cardiac interval that is longer than the immediately preceding cardiac interval as being indicative of cardiac deceleration, and assessing the level of parasympathetic tone based on the cardiac intervals that are identified as being indicative of cardiac deceleration; and (c.2) assessing the patient's level of sympathetic tone in one of the following manners (c.2.i) determining the patient's average cardiac interval based on the measured cardiac intervals, and assessing the level of sympathetic tone based on the determined average cardiac interval;

(c.2.ii) determining the patient's average heart rate based on the measured cardiac intervals, and assessing the level of sympathetic tone based on the determined average heart rate; and (c.2.iii) identifying each said cardiac interval that is shorter than the immediately preceding cardiac interval as being indicative of cardiac acceleration, and assessing the level of sympathetic tone based on the cardiac intervals that are identified as being indicative of cardiac acceleration.

2. For use with an implantable device, a method for independently monitoring levels of parasympathetic and sympathetic tone of a patient, comprising:

(a) sensing a cardiac electrogram (EGM) signal using implanted electrodes;

(b) measuring cardiac intervals within a portion of the sensed EGM signal; and (c) independently assessing levels of parasympathetic tone and sympathetic tone based on the measured cardiac intervals, wherein step (c) includes:

(c.1) identifying each said cardiac interval that is longer than the immediately preceding cardiac interval as being indicative of cardiac deceleration; and (c.2) assessing the level of parasympathetic tone based on the cardiac intervals that are identified as being indicative of cardiac deceleration.

3. The method of claim 2, wherein step (c) further includes:

(c.3) identifying each said cardiac interval that is shorter than the immediately preceding cardiac interval as being indicative of cardiac acceleration; and (c.4) assessing the level of sympathetic tone based on the cardiac intervals that are identified as being indicative of cardiac acceleration.

4. For use with an implantable device, a method for independently monitoring levels of parasympathetic and sympathetic tone of a patient, comprising:

(a) sensing a cardiac electrogram (EGM) signal using implanted electrodes;

(b) measuring cardiac intervals within a portion of the sensed EGM signal; and (c) independently assessing levels of parasympathetic tone and sympathetic tone based on the measured cardiac intervals, wherein step (c) includes:

(c.1) identifying each said cardiac interval that is longer than the immediately preceding cardiac interval as a positive anchor point;

(c.2) defining for each identified positive anchor point a segment of at least three consecutive said cardiac intervals that is generally centered about the positive anchor point;

(c.3) averaging the segments defined for the positive anchor points to produce an average deceleration segment; and (c.4) assessing a level of parasympathetic tone based on the average deceleration segment.

5. The method of claim 4, wherein step (c) further includes:

(c.5) identifying each said cardiac interval that is shorter than the immediately preceding cardiac interval as a negative anchor point;

(c.6) defining for each identified negative anchor point a segment of at least three consecutive said cardiac intervals that is generally centered about the negative anchor point;

(c.7) averaging the segments defined for the negative anchor points to produce an average acceleration segment; and (c.8) assessing the level of sympathetic tone based on the average acceleration segment.

6. The method of claim 5, wherein:

step (c.4) includes determining a metric indicative of an amplitude of a parasympathetic central wavelet of the average deceleration segment; and assessing the level of parasympathetic tone based on the metric of the parasympathetic central wavelet; and step (c.8) includes determining a metric indicative of an amplitude of a sympathetic central wavelet of the average acceleration segment; and assessing the level of sympathetic tone based on the metric of the sympathetic central wavelet.

7. The method of claim 6, wherein:

step (c.4) further includes recognizing a decrease in the metric of the parasympathetic central wavelet of the average deceleration segment as being indicative of a decrease in parasympathetic tone; and recognizing an increase in the metric of the parasympathetic central wavelet of the average deceleration segment as being indicative of an increase in parasympathetic tone; and step (c.8) further includes recognizing a decrease in the metric of the sympathetic central wavelet of the average acceleration segment as being indicative of a decrease in sympathetic tone; and recognizing an increase in the metric of the sympathetic central wavelet of the average acceleration segment as being indicative of an increase in sympathetic tone.

8. The method of claim 5, wherein:

step (c.4) includes determining a time constant of the average deceleration segment; and assessing the level of parasympathetic tone based on the time constant of the average deceleration segment; and step (c.8) includes determining a time constant of the average acceleration segment; and assessing the level of sympathetic tone based on the time constant of the average acceleration segment.

9. The method of claim 8, wherein:

step (c.4) further includes recognizing a decrease in the time constant of the average deceleration segment as being indicative of a decrease in parasympathetic tone; and recognizing an increase in the time constant of the average deceleration segment as being indicative of an increase in parasympathetic tone; and step (c.8) further includes recognizing a decrease in the time constant of the average acceleration segment as being indicative of an increase in sympathetic tone; and recognizing an increase in the time constant of the average acceleration segment as being indicative of a decrease in sympathetic tone.

10. The method of claim 5, wherein:
step (c.4) includes
determining a slope of the average deceleration segment, and
assessing the level of parasympathetic tone based on the slope of the average deceleration segment; and
step (c.8) includes
determining a slope of the average acceleration segment; and
assessing the level of sympathetic tone based on the slope of the average acceleration segment.

11. The method of claim 10, wherein:
step (c.4) further includes
recognizing a decrease in the slope of the average deceleration segment as being indicative of an increase in parasympathetic tone; and
recognizing an increase in the slope of the average deceleration segment as being indicative of a decrease in parasympathetic tone; and
step (c.8) further includes
recognizing a decrease in the slope of the average acceleration segment as being indicative of a decrease in sympathetic tone; and
recognizing an increase in the slope of the average acceleration segment as being indicative of an increase in sympathetic tone.

12. The method of claim 5, wherein step (c) includes:
producing a measurement of the average deceleration segment and a measurement of the average acceleration segment;
normalizing the measurement of the average deceleration segment and the measurement of the average acceleration segment; and
assessing the level of parasympathetic tone based on the normalized measure of the average deceleration segment, and assessing the level of sympathetic tone based on the normalized measure of the average acceleration segment.

13. The method of claim 12, further comprising producing an autonomic nervous system index (ANSi) value based on the normalized measure of the average deceleration segment and the normalized measure of the average acceleration segment.

14. The method of claim 1, further comprising:
comparing the assessed levels of parasympathetic and sympathetic tone for the patient with previously assessed levels parasympathetic and sympathetic tone for the patient to monitor changes in the patient's levels of parasympathetic and sympathetic tone.

15. The method of claim 1, comprising repeating steps (a) through (c) over time to monitor changes in the patient's levels of parasympathetic and sympathetic tone.

16. The method of claim 1, wherein step (c) comprises determining the patient's diurnal variation of cardiac intervals based on the measured cardiac intervals, and assessing the level of parasympathetic tone based on the diurnal variation of cardiac intervals.

17. The method of claim 1, wherein step (c) comprises determining the patient's diurnal variation of heart rate based on the measured cardiac intervals, and assessing the level of parasympathetic tone based on the diurnal variation of heart rate.

18. The method of claim 15, further comprising:
(d) monitoring for diabetic autonomic neuropathy based on the patient's levels of parasympathetic and sympathetic tone.

19. An implantable device for assessing levels of parasympathetic and sympathetic tone of a patient, comprising:
implantable electrodes for sensing a cardiac electrogram (EGM) signal;
means for measuring cardiac intervals within a portion of the sensed EGM signal;
means for independently assessing levels of parasympathetic tone and sympathetic tone based on the measured cardiac intervals, wherein the means for independently assessing levels of parasympathetic tone and sympathetic tone comprises one or more processor, and
wherein the one or more processor assesses the level of parasympathetic tone in one of the following manners:
determining the patient's diurnal variation of cardiac intervals based on the measured cardiac intervals, wherein diurnal variation of cardiac intervals is a measurement of change in cardiac intervals over the course of a day, and assessing the level of parasympathetic tone based on the diurnal variation of cardiac intervals;
determining the patient's diurnal variation of heart rate based on the measured cardiac intervals, wherein diurnal variation of heart rate is a measurement of change in heart rate over the course of a day, and assessing the level of parasympathetic tone based on the diurnal variation of heart rate; and
identifying each said cardiac interval that is longer than the immediately preceding cardiac interval as being indicative of cardiac deceleration, and assessing the level of parasympathetic tone based on the cardiac intervals that are identified as being indicative of cardiac deceleration; and
wherein the one or more processor assesses the level of sympathetic tone in one of the following manners
determining the patient's average cardiac interval based on the measured cardiac intervals, and assessing the level of sympathetic tone based on the determined average cardiac interval;
determining the patient's average heart rate based on the measured cardiac intervals, and assessing the level of sympathetic tone based on the determined average heart rate; and
identifying each said cardiac interval that is shorter than the immediately preceding cardiac interval as being indicative of cardiac acceleration, and assessing the level of sympathetic tone based on the cardiac intervals that are identified as being indicative of cardiac acceleration.

20. The device of claim 19, further comprising:
means for comparing the assessed levels of parasympathetic and sympathetic tone for the patient with previously assessed levels parasympathetic and sympathetic tone for the patient to monitor changes in the patient's levels of parasympathetic and sympathetic tone.

* * * * *